(12) United States Patent
Ducharme et al.

(10) Patent No.: US 8,118,848 B2
(45) Date of Patent: Feb. 21, 2012

(54) ORTHOPEDIC PLATE FOR USE IN FIBULA REPAIR

(75) Inventors: Dustin Ducharme, Stow, OH (US); Bryan D. Den Hartog, Rapid City, SD (US); Derek S. Lewis, Copley, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 418 days.

(21) Appl. No.: 12/380,166

(22) Filed: Feb. 24, 2009

(65) Prior Publication Data

US 2009/0312759 A1    Dec. 17, 2009

Related U.S. Application Data

(63) Continuation-in-part of application No. 11/340,028, filed on Jan. 26, 2006, now Pat. No. 7,771,457.

(60) Provisional application No. 60/648,364, filed on Jan. 28, 2005.

(51) Int. Cl.
*A61B 17/80* (2006.01)
(52) U.S. Cl. .................. 606/291; 606/280; 606/286
(58) Field of Classification Search .............. 606/280, 606/70, 71, 282–286, 291
See application file for complete search history.

(56) References Cited

U.S. PATENT DOCUMENTS

| | | |
|---|---|---|
| 2,526,959 A | 10/1950 | Lorenzo |
| 3,716,050 A | 2/1973 | Johnston |
| 4,867,144 A | 9/1989 | Karas et al. |
| 4,903,691 A | 2/1990 | Heinl |
| 5,304,180 A | 4/1994 | Slocum |
| 5,324,290 A | 6/1994 | Zdeblick et al. |
| 5,569,250 A | 10/1996 | Sarver et al. |
| 5,681,311 A | 10/1997 | Foley et al. |
| 5,690,631 A | 11/1997 | Duncan et al. |
| 5,718,705 A | 2/1998 | Sammarco |
| 5,749,872 A | 5/1998 | Kyle et al. |
| 5,853,413 A | 12/1998 | Carter et al. |
| 6,030,389 A | 2/2000 | Wagner et al. |
| 6,096,040 A | 8/2000 | Esser |
| 6,123,709 A | 9/2000 | Jones et al. |
| D449,692 S | 10/2001 | Michelson |
| 6,358,250 B1 | 3/2002 | Orbay |
| 6,454,769 B2 | 9/2002 | Wagner et al. |

(Continued)

FOREIGN PATENT DOCUMENTS

CH        611147 A5        5/1979

(Continued)

OTHER PUBLICATIONS

Locking Clavicle Plate System by ACUMED® Jul. 2005, (7 pages).

(Continued)

*Primary Examiner* — Eduardo C Robert
*Assistant Examiner* — Ellen C Hammond
(74) *Attorney, Agent, or Firm* — Hudak, Shunk & Farine Co. LPA

(57) ABSTRACT

The present invention relates to an orthopedic plate for use in repair of a fibula. The plate has a Y-shaped profile which has the contour of a spoon where the bowl includes a terminal pair of arms that form differing angles and lengths relative to the trunk portion of the plate. The arms include locking screw holes where the screws converge toward each other, but do not impinge so as to provide-multiplanar fixation.

3 Claims, 4 Drawing Sheets

U.S. PATENT DOCUMENTS

| | | | |
|---|---|---|---|
| 6,527,776 B1 | 3/2003 | Michelson | |
| 6,565,570 B2 | 5/2003 | Sterett et al. | |
| 6,575,975 B2 | 6/2003 | Brace et al. | |
| 6,585,769 B1 | 7/2003 | Muhanna et al. | |
| 6,623,486 B1 | 9/2003 | Weaver et al. | |
| D520,637 S | 5/2006 | Kay et al. | |
| 7,052,499 B2 | 5/2006 | Steger et al. | |
| 7,108,697 B2 | 9/2006 | Mingozzi et al. | |
| 7,128,744 B2 | 10/2006 | Weaver et al. | |
| 7,166,111 B2 | 1/2007 | Kolb et al. | |
| 7,341,589 B2 | 3/2008 | Weaver et al. | |
| 7,776,076 B2 * | 8/2010 | Grady et al. | 606/291 |
| 2003/0199875 A1 | 10/2003 | Mingozzi et al. | |
| 2004/0193163 A1 | 9/2004 | Orbay | |
| 2005/0015089 A1 | 1/2005 | Young et al. | |
| 2006/0129151 A1 | 6/2006 | Allen et al. | |
| 2006/0173458 A1 | 8/2006 | Forstein et al. | |
| 2006/0173459 A1 | 8/2006 | Kay et al. | |
| 2006/0200145 A1 | 9/2006 | Kay et al. | |
| 2006/0212035 A1 | 9/2006 | Wotton, III | |
| 2006/0235411 A1 | 10/2006 | Blain et al. | |
| 2006/0241608 A1 * | 10/2006 | Myerson et al. | 606/69 |
| 2007/0043366 A1 * | 2/2007 | Pfefferle et al. | 606/69 |
| 2007/0073298 A1 | 3/2007 | Beutter et al. | |
| 2007/0185493 A1 | 8/2007 | Feibel et al. | |
| 2007/0233106 A1 | 10/2007 | Horan et al. | |
| 2008/0051786 A1 | 2/2008 | Jensen | |
| 2008/0300632 A1 | 12/2008 | Butler et al. | |
| 2008/0300637 A1 | 12/2008 | Austin et al. | |

FOREIGN PATENT DOCUMENTS

| | | |
|---|---|---|
| DE | 203 09 361 U1 | 5/1979 |
| EP | 1 468 655 A2 | 10/2004 |
| FR | 2 233 973 A1 | 2/1975 |
| FR | 2 405 062 A1 | 6/1979 |
| FR | 2 405 705 A1 | 6/1979 |
| FR | 2 405 706 A1 | 6/1979 |
| JP | 11299804 | 11/1992 |
| WO | WO 02/096309 A1 | 12/2002 |
| WO | WO 2004/086990 A1 | 10/2004 |

OTHER PUBLICATIONS 3.5 mm LCP Superior Anterior Clavicle Plates, by SYNTHES® Sep. 2008 (24 pages).

PERI-LOC Locked Plating System—Clavicle Locking Plate by Smith&Nephew, May 2007 (16 pages).

Locking Bone Plate System for Hallux-Valgus Corrections "Opening or Closing Base Wedge" Osteotomy by MetaFix™ Feb. 2005 (2 pages).

4 pages from INTEGRA™ Jan. 2005 new deal®, Hallu®—S PLATE.

TOM™-Platee by DARCO® Innovation in Foot Care Technology, Dec. 8, 2006 (2 pages).

New Trauma Products from AO Development, Jun. 2006 (p. 6).

6 pages from the Reconstructive Surgery Product Catalog 2005 INTEGRA ™ new deals®, New Ideas for foot surgery™, including p. 18 Neweal—Hallu®—Fix.

* cited by examiner

ORTHOPEDIC PLATE FOR USE IN FIBULA REPAIR

CROSS-REFERENCE

This application is a Continuation-in-Part application based on U.S. patent application Ser. No. 11/340,028 filed on Jan. 26, 2006 and on U.S. Provisional Application Ser. No. 60/648,364 filed on Jan. 28, 2005.

FIELD OF THE INVENTION

The present invention relates to an orthopedic plate in particular for surgical repair or reconstruction of a fibula and to a method for its use.

BACKGROUND OF THE INVENTION

The field of orthopedic medicine has grown tremendously in the past fifty years as surgical techniques, implants and instrumentation have developed and been improved. The small bones are frequently subject to the need for re-constructive surgery for example, as a result of trauma, to counteract the effects of aging or to repair congenital deformities and trauma and spinal areas. While there is a wide variety in the exact shape and mass of all bones, these variations become more problematic in providing orthopedic implants for small bone applications since there is less room on and about the bone for the surgeon to place and fix the construct. These bones are finer and have less surface area for placement of an implant, and less mass for the placement of screws and as a result, individual variations become more problematic for orthopedic plates of stock design. Consequently, surgeons have tended to rely on the use of screws and wires for reconstruction or have had to resort to operating room contouring procedures which can weaken the plates and/or distort the screw holes within the plates. This is a particular problem in instances in which either variable locking mechanisms are used, or in which locking screws are used with the plates. None-the-less, locking screws often are used to advantage as they provide more secure placement of the screws in the bone, cause better compression through a fractures, and can be less likely to harm the bone or back out of the plate.

One problem that needs to be avoided in the delicate environment of the small bone area is the interference of screws, with other screws, and with the function of ligaments and tendons. While it may be desirable to design an orthopedic plate so that securing screws converge in order to cause compression or increase the pullout strength, it is difficult when a screw impinges on or conflicts with the desired placement of another screw. Some surgeons prefer bicortical fixation in which a screw is sized so that the distil end is secured in cortical bone giving the screw better purchase, however, other surgeons may prefer to avoid placing a screw so that it projects beyond the outer surface of the anchoring bone. These factors are complicated by the relative lack of soft tissue and the presence of ligaments and tendons in the small bone areas. Consequently, the less forgiving biological environment in which the small bone surgeon works requires greater procedural precision and calls for specialized implants and tools.

The present invention is designed to meet the specific needs of the small bone surgeon to facilitate effective and repeatable procedures which provide for ease of use and a range of function for this specific area of specialization. The present invention is specifically intended to provide for the treatment of fracture repair following trauma in an otherwise healthy individual where plates are used to maintain the integrity of the bones while they heal, although it is certainly possible that they may also be used for other surgeries such as reconstruction to correct congenital or age related deformation.

The plate is designed specifically for use on the lateral aspect of the fibula, and in particular for the repair of TYPE B, transsyndesmotic fractures. These fractures typically occur when the foot is subjected to axial loading and is in supination, such as can happen during a skiing accident. The talus rotates externally and the fibula fails which results in an oblique fracture beginning at the ankle joint and extending proximally from anterior to posterior. The fracture often also includes fracture of the posterior malleolus or injury of the syndesmotic ligament, and in more extreme cases with a medial failure marked by a rupture of the deltoid ligament of a transverse fracture of the medial malleolus.

The present invention provides a plate with bilaterally asymmetry (meaning that the left half of the plate is not exactly the same as the right half of the plate taken from the medial axis) and with bi-planar screw fixation (meaning that the screws do not lie in a single plane) and further which is designed to facilitate three dimensional contouring to accommodate individual variation in bone shape. The plate is configured to bend laterally, longitudinally, and to wrap or spiral about its longitudinal axis so that it can be molded to an optimal shape for small bone procedures. The plate is designed to provide optimal stabilization of fractures and osteotomies by providing multi-planar fixation that allows for better pull-out and limited axial loading to the bone. The plate is further designed to accelerate fusion success by reducing or eliminating torsional or twisting stresses to the bone segments during the healing process. In addition, when desired, the plate can be shaped so as to apply a compressive, or even a tensile, force, for example, along the longitudinal axis of a bone.

The plate is provided in a number of variations in a surgical tray, for example which include various lengths of the central trunk portion and the number of screw holes in the trunk. This allows the surgeon to select a plate during surgery after opening the wound area and considering the plating needs.

The plate has an elongate central trunk portion including one or more screw holes separated from each other by a waist shaped linking portion along a longitudinal axis. The plate further has a set of arms including screw holes which are placed at an equal distance from the longitudinal axis but which diverge asymmetrically from the longitudinal axis to avoid conflicts in the screw placement of the paired arm, specifically, so that the screws of a set of arms avoid impinging on each other. The plate is radiused about the inferior surface, (i.e. the surface which faces toward and which may, but does not have to fully contact the bone), with a curvature corresponding generally to the curvature of a bony surface. The pair of arms continue this curvature and the through holes are placed so that the angle of the longitudinal axis of the screws converge in the direction of the distil end of the screw. The screw holes are placed with the longitudinal axis perpendicular to a tangent to the top surface of the arm with the effect that the longitudinal axes of the screws converge in the direction of the distil end. The convergence of the screw holes increases the pull-out strength of the screws.

Further the screw holes are rounded and the corresponding mating heads of the screws are rounded and have a low profile so that the screws can be seated with their longitudinal axes at a variety of angles. Preferably, there is at least 20° of conical rotation, and more preferably 25°, and most preferably 30° of conical rotation of the screw axis in relation to the longitudinal axis of the screw hole (i.e. the longitudinal axis of the screw can be rotated through a conical shape about the axis of the screw hole where the apex of the cone describes an angle of 30°). Alternatively, the screw holes can include internal threads which mate with external threads on the head of the screws to cause locking of the screws relative to the plate.

While the screws are at convergent angles, the screws typically do not in fact impinge on each other, or conflict in their placement since each of the arms of the plate in a pair form a different angle to the central trunk so that the longitudinal axis of the screws are offset from each other along the length of the plate. The radiused configuration of the plate is designed to increase operating room efficiency by facilitating commonly desirable shapes while maintaining the required strength and by permitting bending without deforming the screw holes. This results in making customization in anticipation or during surgery easier.

The screws useful with the plate of the present invention are self-starting, self-tapping screws including the option of partial or full cannulation. The screws include a unique cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess that may be a hexagon, a torx shape, or a modification of a torx shape, i.e. a multilobe shape having from 3 to 12 lobes, and preferably having 4 to 8 rounded recesses or lobes. The recess can be of a constant size in the direction of the longitudinal axis, or can taper inward along the longitudinal axis of the screw toward the bottom of the recess. The screws have a low profile, head which is rounded at the junction of the head and the shaft, and also rounded from the maximum diameter toward the top surface or the proximal end relative to the insertion tip, which includes the torque driving recess. This rounded low profile head keeps the screw from having any sharp projecting edges which could provide an irritation to the tissue in the vicinity of the plate and further seats in the plate so that no more than 10% by volume of the screw head projects from the plate.

The instruments for use with the system are well-balanced and ergonomically designed with sufficiently long handles to place the surgeon's hands outside of the line of radiation and designed to reduce fatigue in the operating room.

The plate system of the present invention is thus designed to fit a range of needs of the surgeon operating on the small bones to allow him or her to perfect a variety of techniques using a set of instruments and a customizable plate and screw construct.

DETAILED DESCRIPTION OF THE INVENTION

Figure 1:
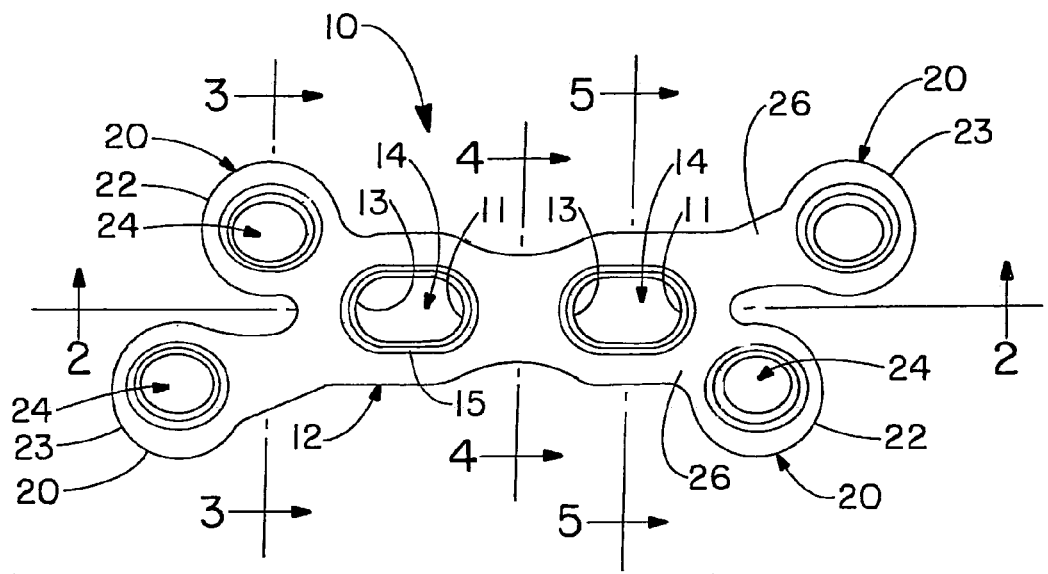
FIG. 1 is a top view of a first embodiment of an orthopedic plate in accordance with the invention.
Figure 2:
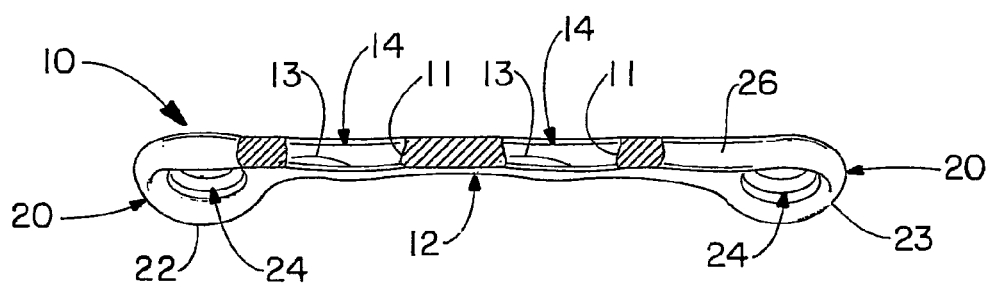
FIG. 2 is a cross-section of the plate of FIG. 1 taken along line 2-2.

The plate 10 of the present invention is shown having a bilaterally asymmetric shape with either one or two pairs of legs extending from a central trunk portion 12 defining the longitudinal axis of the plate. As shown the trunk portion 12 includes two screw holes or slots 14 along the longitudinal axis. However, as can be seen from FIGS. 12 through 18 the plate can be presented in a version which has a plurality of screw holes, for example up to 8 or more. The number of screw holes in the trunk portion 12 will depend on the length of the plate, and may range from 0 to 8, and more preferably from 2 to 4. In one embodiment these holes are compression holes or translation slots. The compression holes 14 are preferably slotted or elongated and optionally may have a larger radius area 11 on each of the screw holes facing in the same direction, and a smaller radius area 13 in order to induce a compression toward the smaller radius end. The holes may also or alternatively have a shallow shoulder or lip 18 which descends toward the inferior surface of the plate to allow the plate to be set initially and subsequently to be slide into a different position as the screws are tightened down. This allows compression to be applied across the middle of the trunk section. The plates include a visual indicator of the direction of the compression, such as an arrow 17. Further, the screw holes can include annular rings of increased thickness in the vertical direction about through holes 14.

The through holes 14 in the trunk portion 12 have a longitudinal axis that is perpendicular to plane tangent to the top radius of the plate. The area linking the screw holes has a decreased width so as to define a waist area 26 that will bend laterally (or "curve") relative to the longitudinal axis and which will bend longitudinally to form a curved area in and out of the plane of the plate. This thinner area also facilitates twisting of the plate so as to allow the plate to spiral, or wrap around it longitudinal axis. The increased annular area around the through bores resists deformation when a bending device is used to apply a force to the plate through the screw holes.

The plate 10 also includes at least one set of arms 20. As viewed in FIG. 1, these sets of arms can be viewed as a set of a short 22 and a long arm 23. Each of the arms in a set includes screw holes 24 which are placed at a radially equal distance but which diverging asymmetrically from the longitudinal axis of the plate 10. More specifically, each set of arms includes one arm that defines a smaller angle of divergence a from the longitudinal axis of the trunk portion than the angle of divergence of the other arm β. For example, the first angle shown in FIG. 1 at a may be from about 5° to about to 25°, and more preferably from about 10° to about to 20° and most preferably from about 12° to about to 16°, while the second angle shown at β from about 10° to about to 35°, and more preferably from about 15° to about to 30° and most preferably from about 22° to about to 26° with a preferred difference in the angles beings from about 2° to about to 20°, and more preferably from about 4° to about to 16° and most preferably from about 8° to about to 12°.

In addition to the angled arms of this asymmetrical shape facilitating a variety of useful positions in the small bone area, the plate of the present invention is sized to fit the needs of the small bone specialist. For small bone usage, the total length of the plate along its longitudinal axis is from about 25 mm to about 80 mm, depending on the number of screw holes in the trunk portion. The total width is from about 12 mm to about 18 mm, width an inferior radius of curvature of about 8 mm to about 12 mm and a concentric radius on the superior side. Typically, the waist area measures from about 7.5 mm to about 10 mm from the center of the larger, i.e. about 3.8 mm, radiused portion of the holes. The trunk portion has a width of about 7 mm to about 9 mm wide at the wider parts and about 3 mm to about 5 mm wide at the narrower waist portion. The longer arm has a length along the longitudinal axis of the plate from the center of the screw hole to the center of the plate for a two-hole trunk of from about 12 mm to about 16 mm, with a width of about 3 mm to about 5 mm. The shorter arm has a comparable length of from about 7 mm to about 15 mm with a narrowed width of about 2.5 to about 5 mm. In a further embodiment the plate could be modified for use in the long bones with a length of up to about 400 mm with a width of up to about 50 mm, and proportional sizes for the arms and thickness.

On the inferior side, or the side that would be facing (which contemplates opposing or touching or partially touching the) bone surface in use, the arms continue the radius of curvature of the trunk portion. The superior or top side of the plate has a similar radius of curvature as the top surface of the plate has an outline that corresponds with the shape of the bottom of the plate (excluding the optional thickened annular area surrounding the screw holes which would act to shield these holes against deformation during bending.) The screw holes also include a rounded concavity to mate with the rounded shape of the head of the screw to allow of variable axis positioning. The screw holes 24 are placed with the longitudinal axis perpendicular a tangent to the top surface of the arm with the effect that the longitudinal-axes of the screws converge in the direction of the distil end. This increases the pull-out strength of the plate/screw construct. Since the arms are asymmetrical relative to each other, and in particular since they diverge from the longitudinal axis of the trunk portion at differing angles, conflicts in the positions of paired screws is avoided so that the screws of a set of arms typically do not impinge on each other. This is even more important in instances where the plate is bent around the longitudinal axis so as to wrap around the longitudinal axis of the bone.

The arms 20 also each include a screw hole 24 which, like the trunk portion 12 has a linking portion 26 that joins the screw hole to the trunk portion. Again this design facilitates the desired bending while resisting deformation of the screw holes 24 when they are used with the bending instrument to contour the plate. The angle of the arms 20 of each one of a pair of arms (both top and bottom and right and left pairs) varies so as to create a bilateral asymmetry, meaning that the plate is not symmetrical with respect to a plane that passes through the longitudinal axis in the vertical direction from the superior (the top side relative to the bone) to the inferior side (the side facing the bone), the "first plane".

Figure 3:
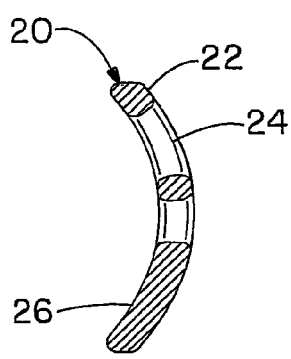
FIG. 3 is a cross-section of the plate of FIG. 1 taken along line 3-3.
Figure 4:
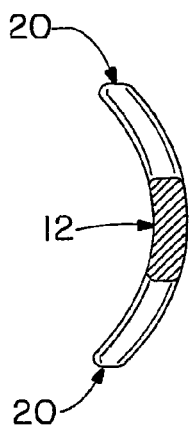
FIG. 4 is a cross-section of the plate of FIG. 1 taken along line 4-4.
Figure 5:
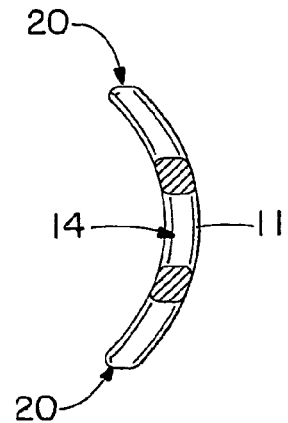
FIG. 5 is a cross section of the plate of FIG. 1 taken along line 5-5.

The screws holes of the trunk portion can include means to induce a compressive force in one direction, such as a ramped area on each screw hole. These ramped areas would be ramped on the same side of the holes looking down from the top of the plate. Typically the first screw implanted stabilizes and the second screw is used to achieve compression. Further the length of each of the arms of a pair will vary so that the radial length of the center of the screw hole to the intersection with the longitudinal axis will be the same. As shown in FIGS. 3-5, the plate includes a radial curve about the longitudinal axis. The radius is typically about 10 mm with a transverse dimension from the edge of one arm to the edge of the other arm of a pair being about 15 or 16 mm for typical small bone usage, and the screw bore having a longitudinal axis of about 24° to a plane passing through the longitudinal axis of the plate. The bores are typically about 3.75 mm for a 3.5 mm diameter screw for small bones excluding the smallest of applications which would include phalanges. Again, for the smallest application as well as long bone embodiments the screws and corresponding screw holes could be sized to range from a 1.5 mm diameter screw up to a 7.5 mm diameter screw. In a further embodiment, the bore could be threaded.

Figure 6:
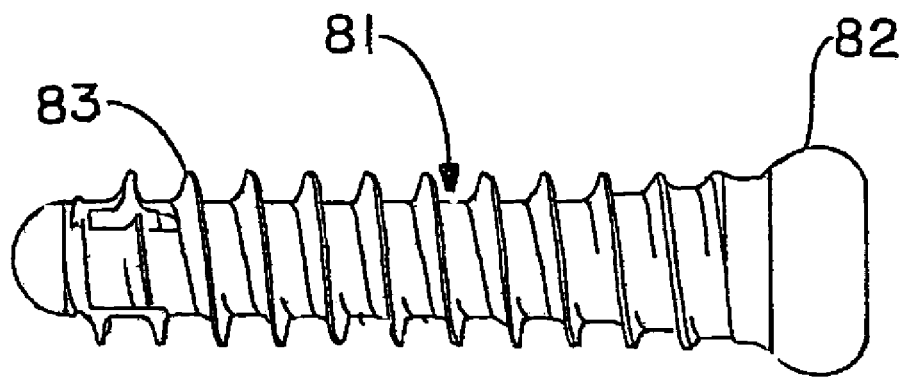
FIG. 6 is a side view of a screw used with the present system.
Figure 7:
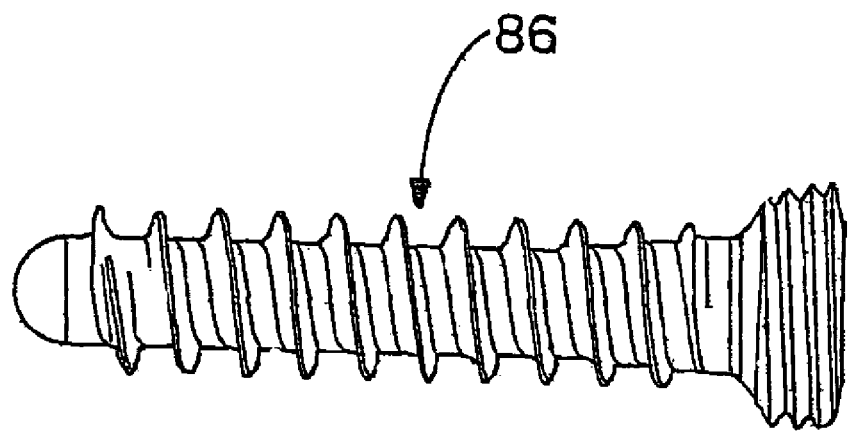
FIG. 7 is a side view of a locking screw used with the present invention

FIG. 6 shows a screw 81 which could be used with the plate system of the present invention. The distil end of the screw can include a cutting tip which is self-starting and self-tapping or a rounded blunt tip. This aspect is defined by a conical recess and a plurality of flutes. These screws 81 can optionally include partial or full cannulation. The head of the screw 82 is spherical and includes a torque driving recess, such as a modified multilobe shape. The screw has a cancelleous thread 83 with a constant major diameter and a minor diameter that tapers proximally in order to increase fatigue life of the screw and to improve compression and compensate for bone resorption. FIG. 7 shows a locking screw 86 which could be used with the present invention. The screw includes the same features as the screw in FIG. 6, except that the screw further includes external threads 88 on the screw head.

Figure 8:
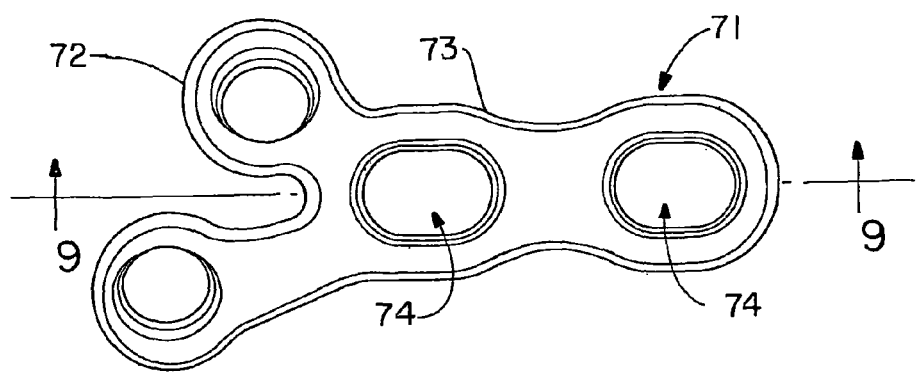
FIG. 8 is a top view of a first version of a second embodiment of the plate in accordance with the invention
Figure 9:
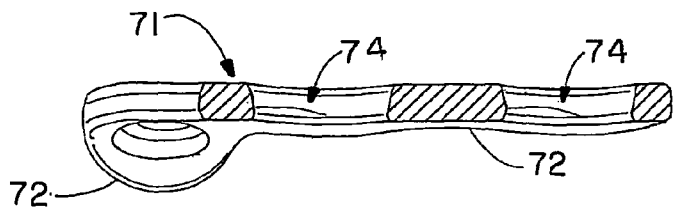
FIG. 9 is a cross section of the plate of FIG. 8 taken along line 9-9.
Figure 10:
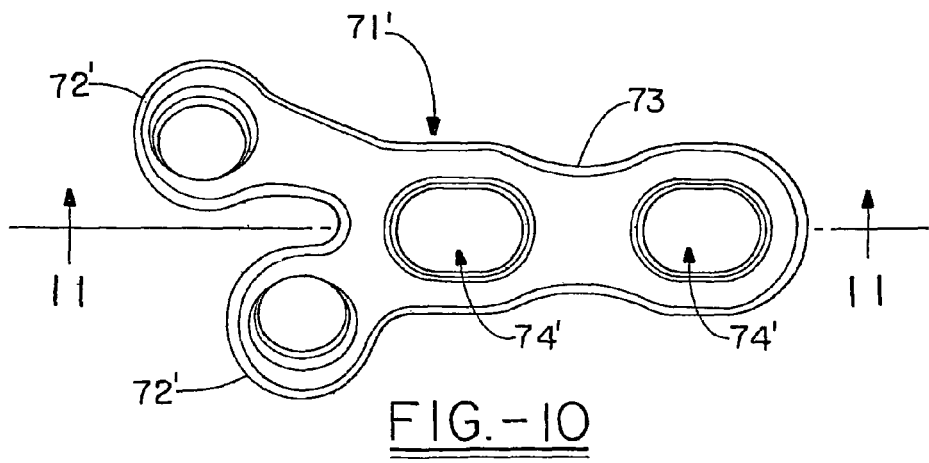
FIG. 10 is a mirror version of the plate shown in FIG. 8.
Figure 11:
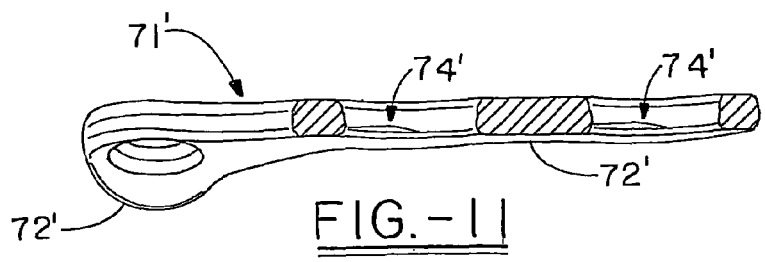
FIG. 11 is a cross section of the plate of FIG. 10 taken along line 10-10.
Figure 12:
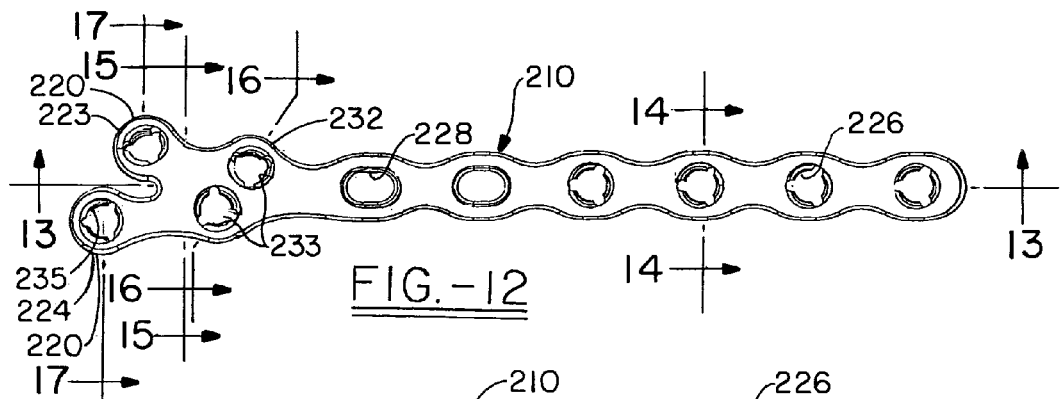
FIG. 12 is a top view of a left version of a third embodiment of a plate in accordance with the invention.
Figure 13:
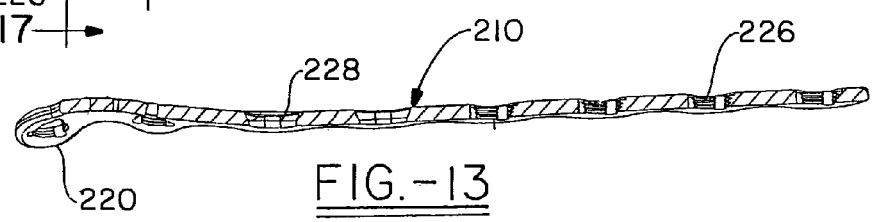
FIG. 13 is a cross section of the plate of FIG. 12 taken along line 13-13.
Figure 15:
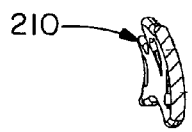
FIG. 15 is a cross section of the plate of FIG. 12 taken along line 15-15.
Figure 14:
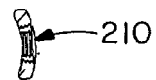
FIG. 14 is a cross section of the plate of FIG. 12 taken along line 14-14.
Figure 16:
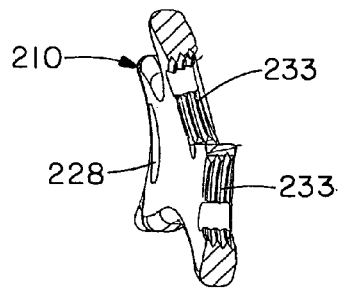
FIG. 16 is a cross section of the plate of FIG. 12 taken along line 16-16.
Figure 17:
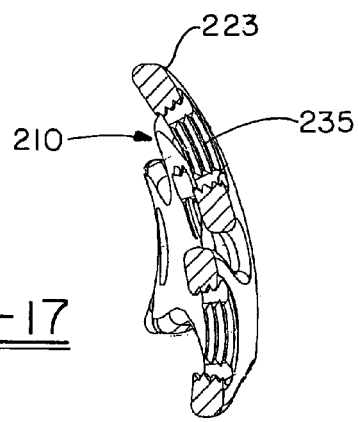
FIG. 17 is a cross section of the plate of FIG. 12 taken along line 17-17.
Figure 18:
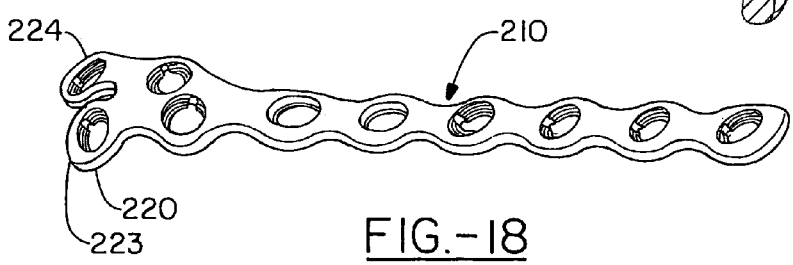
FIG. 18 is a perspective view of the plate of FIG. 12.

FIGS. 8 through 11 show a second embodiment of a plate in accordance with the present invention in which the plate shown in FIG. 10 is a mirror image of the plate shown in FIG. 8. In this embodiment, the plate 71, 71' has a Y-shape with an elongate and cylindrical central trunk having a single pair of arms 72, 72' extending as previously described from the a trunk portion 73, 73'. The trunk portion optionally has one or more compression slots 74,74'.

FIGS. 12 through 18 show an embodiment of the present invention which has a Y-shaped profile similar to the embodiment shown in FIGS. 8 and 10. This embodiment is designed especially to repair a type B: transsyndesmotic fracture of the fibula. The plate 210 has a central trunk portion 212 which includes one or more through holes and a single pair of divergent and laterally offset arms 220. In particular, the trunk can include both screw holes 226 and obround holes 228 which can be compression slots or translations slots which are used for initial fixation and which subsequently allow for translation of the plate relative to that fixation. Further the central trunk 212 has a linear medial longitudinal axis and at least a portion has a constant radial curve toward the bone-facing side of the plate. Thus, at least a portion of the central trunk is a segment of a cylinder. The plate 210 has a pair 220 of arms 223,224 that extend as previously described. Specifically, each of the arms 223 and 224 include a screw hole 235 which defines an axis of the screw (perpendicular to a tangent at the diameter of the screw hole) and the arms have a longitudinal axis which is a line intersecting the screw axis and the longitudinal axis of the central trunk as medial as possible to the arm. For each arm, the longitudinal axis defines an angle relative to the longitudinal axis of the central trunk, and the angle is different for one arm than for the other arm.

In this embodiment, the central trunk widens adjacent the arms to form a neck area 232, which can have a screw hole, or, more preferably, two screw holes 233 which are offset from the longitudinal axis and the screw hole on the same side as the longer of the two arms is distally in advance of the other neck screw holes.

As has been previously described, the pair of arms include an inferior curve in the same direction (although not necessarily of the same size) as the radial curve in the central trunk portion. The plate bows in a superior direction and the curve widens so that the topography of the plate is like a spoon with a neck connecting the handle and the bowl of the plate, and the arms form a portion of the bowl of the spoon. The difference in the length and angles of the arms allows for multiplanar fixation and convergence of the screws (which are locking screws) while avoiding impingement of the screws with each other. Thus, the plate is designed to fit the lateral malleolus and the arms are designed to cup and wrap around the ankle bone. The plate is shown with two obround slots in the central trunk and four locking screw holes that include internal threads and keyways for a drill guide to set the angles for the screws. The plate can have one or no slots and from 1 to 8 screw holes. Further, the plate can include a terminal set of arms as is shown in FIG. 1.

While in accordance with the patent statutes, the best mode and preferred embodiment have been set forth, the scope of the invention is not limited thereto, but rather by the scope of the attached claims.

What is claimed is:

1. A surgical plate system, comprising:
   a pre-contoured Y-shaped plate that has an inferior surface and which has a concentric superior surface, the plate consisting of a trunk and a pair of a first arm and a second arm,
   the trunk having a linear medial longitudinal axis along the superior surface extending between a first and a second end, and the inferior surface of the plate defining a curve transverse to the medial axis, the trunk including at least one screw hole and,
   the first arm and the second arm extending from the first end of the trunk, the inferior surface of the first arm and of the second arm spiraling around the medial longitudinal axis of the trunk,
   the first arm having an ear with at least one screw hole defining a first screw axis perpendicular to a tangent to the top surface of the first ear, the first ear being attached to the trunk by a linking section, a first angle and a first length being defined by a line from the center of the first arm screw hole to the intersection of the medial longitudinal axis of the trunk, and,
   the second arm having a second ear with at least one second screw hole defining a second screw, axis perpendicular to a tangent to the top surface of the second ear, the second ear being attached to the trunk by a linking section, a second angle and a second length being defined by a line from the center of the second arm screw hole to the intersection of the medial longitudinal axis of the trunk, and
   the first angle and the first length being different from the second angle and the second length whereby the first screw axis and the second screw axis converge toward the inferior side of the plate but do not intersect to allow for multiplanar fixation, and
   the plate system further including at least one screw having a threaded shaft and a head wherein at least one screw hole includes internal threads and the screw head includes corresponding external threads which mate to fix the orientation of the screw in the screw hole at a locked angular orientation of the screw axis, and a drill guide, and the screw hole includes guide keyways which orient the angle, of the drill guide relative to the plate.

2. A surgical plate system as set forth in claim 1 wherein the plate is capable of being used on a fibula.

3. A surgical plate system as set forth in claim 1 wherein the central trunk includes a neck which links the pair of arms to the central trunk and the neck has a complex contour which forms a spoon shape toward the bone facing side.

* * * * *

UNITED STATES PATENT AND TRADEMARK OFFICE
CERTIFICATE OF CORRECTION

| | | |
|---|---|---|
| PATENT NO. | : 8,118,848 B2 | |
| APPLICATION NO. | : 12/380166 | |
| DATED | : February 21, 2012 | |
| INVENTOR(S) | : Ducharme et al. | |

It is certified that error appears in the above-identified patent and that said Letters Patent is hereby corrected as shown below:

In Claim 1, column 8, line 16, delete the "," between "screw" and "axis".

In Claim 1, column 8, line 35, delete the "," between "angle" and "of".

Signed and Sealed this
Seventeenth Day of April, 2012

David J. Kappos
*Director of the United States Patent and Trademark Office*